(12) United States Patent
Scheller

(10) Patent No.: US 7,972,326 B2
(45) Date of Patent: *Jul. 5, 2011

(54) ILLUMINATED LASER PROBE WITH ADJUSTABLE AREA OF ILLUMINATION

(75) Inventor: Gregg D. Scheller, Glencoe, MO (US)

(73) Assignee: Synergetics, Inc., O'Fallon, MO (US)

( * ) Notice: Subject to any disclaimer, the term of this patent is extended or adjusted under 35 U.S.C. 154(b) by 920 days.

This patent is subject to a terminal disclaimer.

(21) Appl. No.: 10/586,017

(22) PCT Filed: Nov. 15, 2004

(86) PCT No.: PCT/US2004/038176
§ 371 (c)(1),
(2), (4) Date: Oct. 26, 2006

(87) PCT Pub. No.: WO2005/048817
PCT Pub. Date: Jun. 2, 2005

(65) Prior Publication Data
US 2007/0191823 A1 Aug. 16, 2007

(51) Int. Cl.
*A61B 18/18* (2006.01)
(52) U.S. Cl. ............... 606/13; 606/15; 606/16
(58) Field of Classification Search ............ 606/13–16; 607/88, 89; 128/898
See application file for complete search history.

(56) References Cited

U.S. PATENT DOCUMENTS

| | | | |
|---|---|---|---|
| 4,984,563 A | 1/1991 | Renaud | |
| 5,281,214 A | 1/1994 | Wilkins et al. | |
| 5,323,766 A | 6/1994 | Uram | |
| 5,356,407 A * | 10/1994 | Easley et al. | 606/4 |
| 5,469,524 A * | 11/1995 | Esch et al. | 385/118 |
| 5,741,225 A | 4/1998 | Lax et al. | |
| 5,785,645 A | 7/1998 | Scheller | |
| 5,855,577 A | 1/1999 | Murphy-Chutorian et al. | |
| 5,855,755 A * | 1/1999 | Murphy et al. | 205/122 |
| RE36,473 E | 12/1999 | Esch et al. | |
| 6,572,608 B1 * | 6/2003 | Lee et al. | 606/15 |
| 6,984,230 B2 * | 1/2006 | Scheller et al. | 606/15 |
| 7,473,249 B2 * | 1/2009 | Scheller et al. | 606/15 |
| 2008/0287938 A1 * | 11/2008 | Scheller et al. | 606/15 |

FOREIGN PATENT DOCUMENTS

| | | |
|---|---|---|
| EP | 0 682 910 A1 | 11/1995 |
| JP | 11009707 | 1/1999 |
| JP | 2002336291 | 11/2002 |
| WO | WO 9641578 | 12/1996 |
| WO | 9948557 | 9/1999 |

* cited by examiner

Primary Examiner — Ahmed M Farah
(74) Attorney, Agent, or Firm — Thompson Coburn LLP

(57) ABSTRACT

An illuminated laser probe primarily designed for ophthalmic surgery provides both illumination light to a surgical site and laser light to the surgical site. The probe has an elongate handle with a tubular tip extending from a distal end of the handle. A length of illumination optic fiber and a length of laser optic fiber extend through the handle and the tip. A mechanism is provided on the handle at a position where the mechanism can easily be manipulated by a finger of a surgeons hand holding the handle. The mechanism is operatively connected with the laser optic fiber and is manipulated to selectively extend a distal portion of the optic fiber from the instrument tip and retract the distal portion of the optic fiber back into the instrument tip.

14 Claims, 4 Drawing Sheets

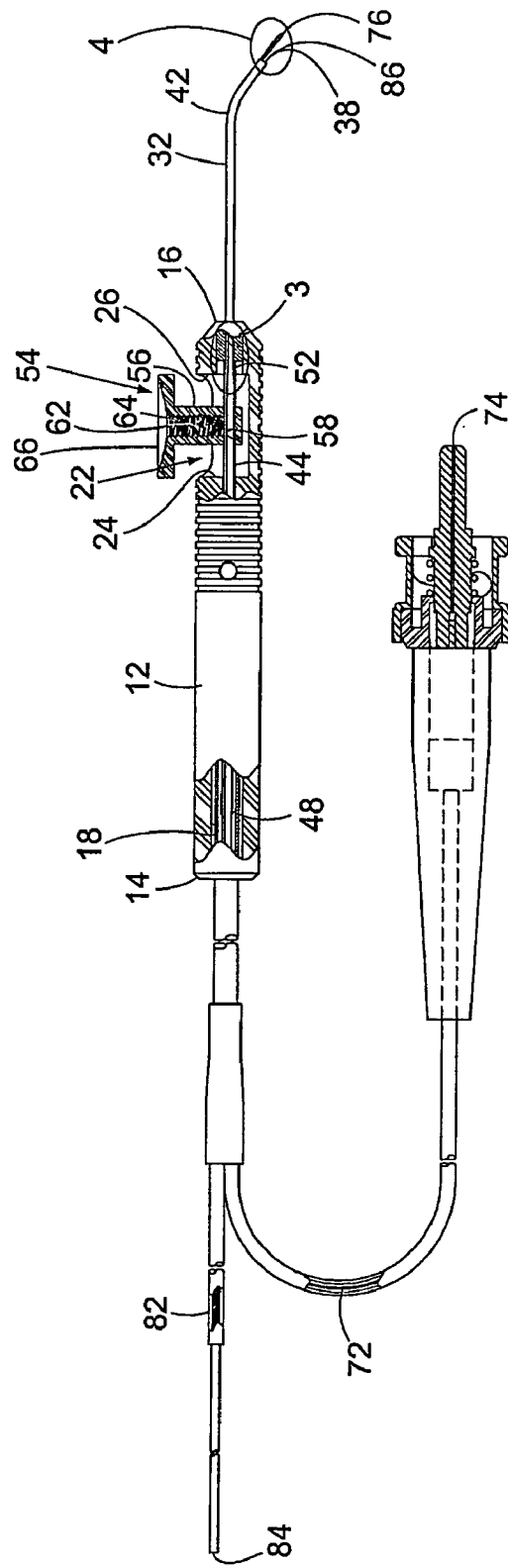
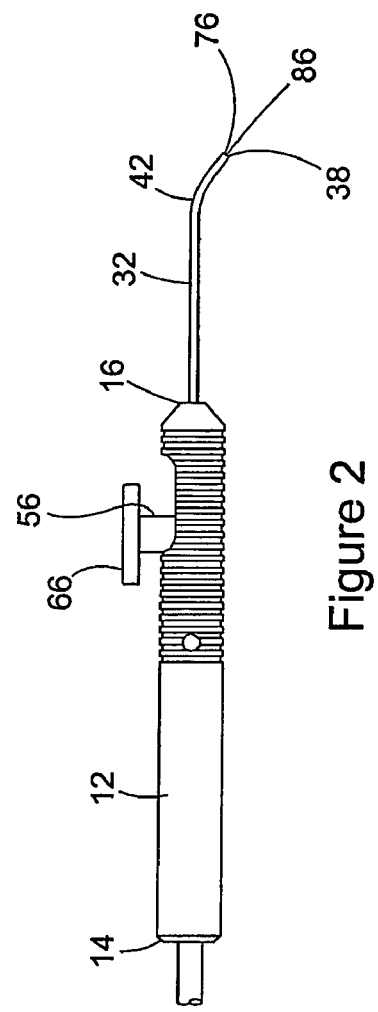
Figure 1
Figure 2

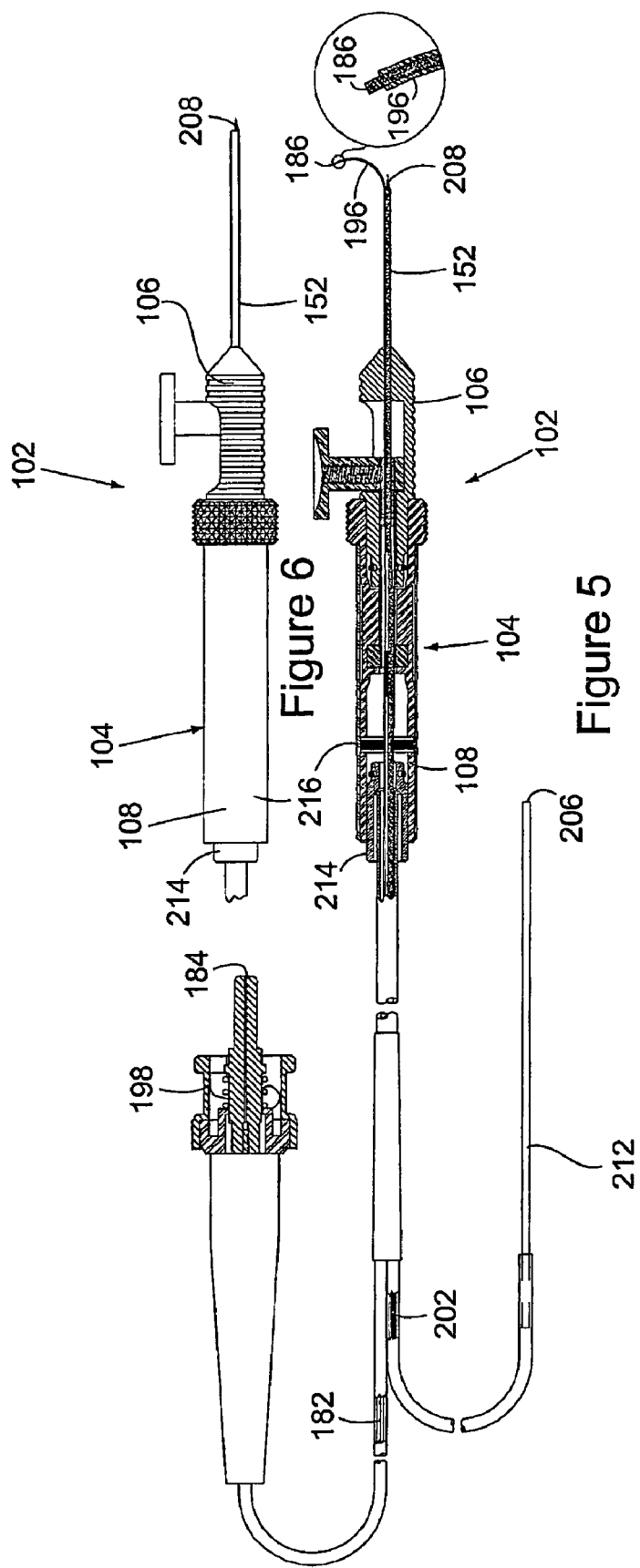

ILLUMINATED LASER PROBE WITH ADJUSTABLE AREA OF ILLUMINATION

FIELD OF THE INVENTION

The present invention pertains to an illuminated laser probe that is primarily designed for ophthalmic surgery procedures where the probe provides both illumination light to a surgical site and laser light to the surgical site.

SUMMARY OF THE INVENTION

The illuminated laser probe of the invention is primarily designed for ophthalmic surgery procedures. The probe provides both illumination light to a surgical site and laser light to the surgical site.

The probe has an elongate manually manipulatable handle. A tubular tip is secured to the handle. The tip projects from the handle to a distal end of the tip.

A length of illumination optic fiber extends through the handle and the tip. The length of illumination optic fiber has opposite proximal and distal ends and the fiber distal end is positioned adjacent the tip distal end. The illumination optic fiber is secured stationary relative to the tip.

A length of laser optic fiber also extends through the handle and the tip. The length of laser optic fiber has opposite proximal and distal ends and the laser optic fiber distal end is positioned adjacent the tip distal end and the illumination optic fiber distal end.

A mechanism is provided on the handle at a position where the mechanism can easily be manipulated by a finger of a surgeon's hand holding the handle. The mechanism is operatively connected to the laser optic fiber to move the laser optic fiber through the handle and the tip between a retracted position of the laser optic fiber where the laser optic fiber distal end is positioned adjacent the tip distal end and the illumination optic fiber distal end, and an extended position of the laser optic fiber where the laser optic fiber distal end is extended from the tip distal end and the illumination optic fiber distal end.

A portion of the laser optic fiber adjacent the laser optic fiber distal end has a curved configuration.

A curved sleeve is mounted on the laser optic fiber distal end portion. The curved sleeve holds the laser optic fiber distal end portion in the curved configuration.

BRIEF DESCRIPTION OF THE DRAWING FIGURES

Features of the invention are set forth in the following detailed description of the preferred embodiment of the invention and in the following drawing figures wherein:

FIG. 1 is a cross section of the surgical instrument of the invention with a laser optic fiber of the instrument extended;

FIG. 2 is a side view of the surgical instrument shown in FIG. 1, with the laser optic fiber retracted;

FIG. 5 is a cross section of a further embodiment of the surgical instrument of the invention with a laser optic fiber of the instrument extended;

FIG. 6 is a side view of the surgical instrument shown in FIG. 5, with the laser optic fiber retracted; and, FIG. 7 is an enlarged view of the cross section of the surgical instrument of FIG. 5.

DETAILED DESCRIPTION OF A PREFERRED EMBODIMENT

Figure 3:
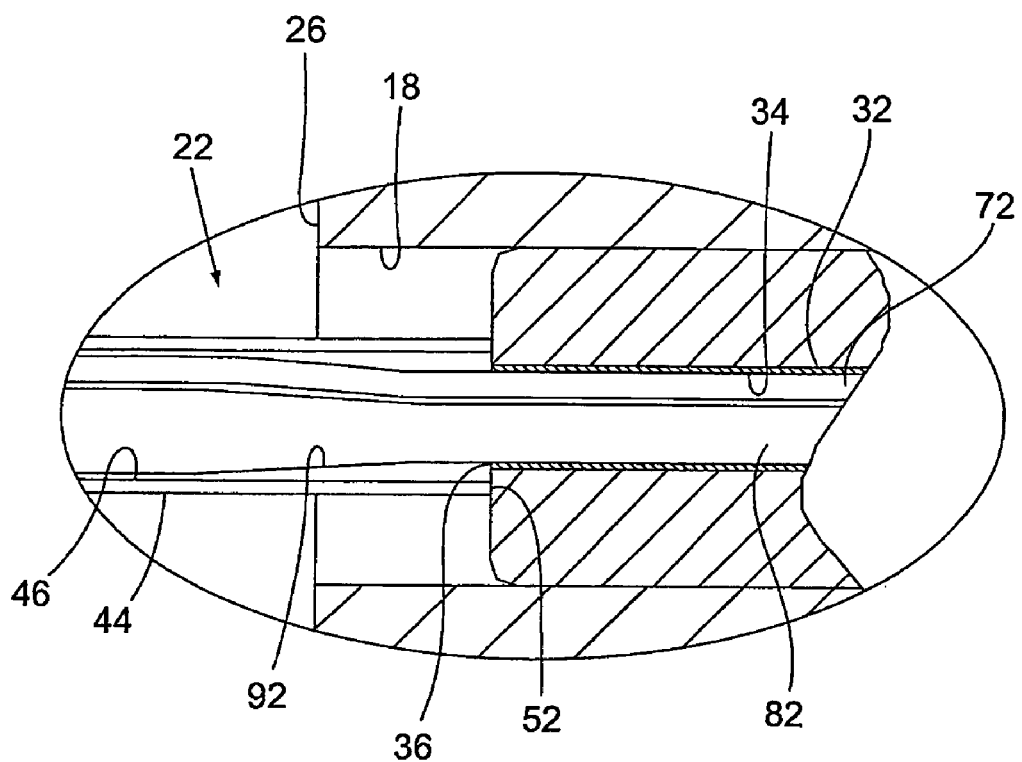
FIG. 3 is an enlarged partial view of the portion of the instrument shown in circle 3 of FIG. 1.
Figure 4:
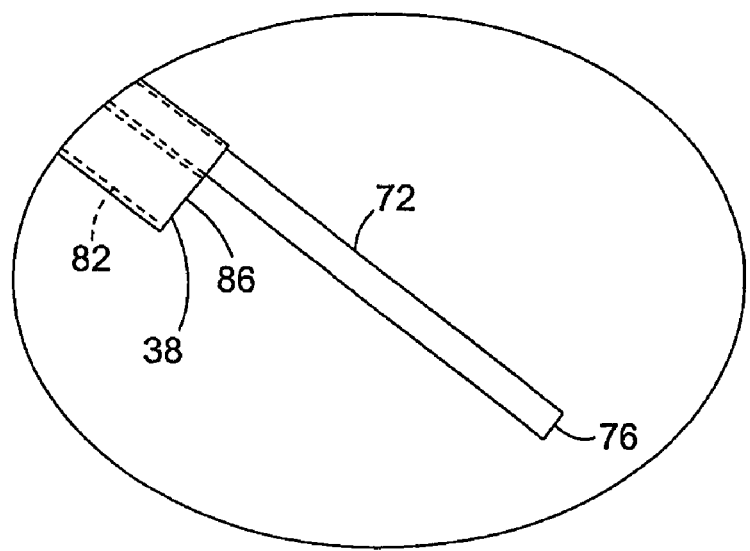
FIG. 4 is an enlarged partial view of the portion of the instrument shown in circle 4 of FIG. 1.

The surgical instrument of the invention is primarily intended to provide illumination light and laser light in laser eye surgery. However, the instrument may be used in other types of surgery. The instrument is designed as a disposable instrument, but alternatively, the instrument could be a reusable instrument that is sterilized after each use.

The instrument has an elongate, narrow handle or hand piece 12 that has opposite proximal 14 and distal 16 ends. The handle 12 is dimensioned to a size similar to that of a pencil to fit comfortably in a surgeon's hand and be easily manually manipulated by the surgeon's hand. A hollow interior bore 18 extends through the center of the handle 12 from the handle proximal end 14 to the handle distal end 16. A cavity 22 is recessed into a side of the handle. The cavity 22 intersects with the handle interior bore 18. The cavity 22 extends along a portion of the length of the handle 12 between a rearward or proximal end 24 of the cavity and a forward or distal end 26 of the cavity.

An elongate, tubular tip 32 projects from the distal end 16 of the handle 12. The tubular tip 32 has an interior bore that extends through the tip from a proximal end 36 of the tip to a distal end 38 of the tip. As seen in FIGS. 1 and 2, the tip 32 has a bend 42 adjacent the tip distal end 38. In alternative embodiments of the instrument, the tip 32 can be straight along its entire length. The tip proximal end 36 is received in the handle interior bore 18 at the handle distal end 16 and is secured stationary in place by adhesives or other equivalent means.

An elongate sleeve 44 is mounted in the handle interior bore 18 for reciprocating movement of the sleeve through the bore. The sleeve 44 has an interior bore 46 that extends through the sleeve from a proximal end 48 of the sleeve to a distal end 52 of the sleeve. As seen in FIGS. 1 and 3, a portion of the sleeve adjacent the sleeve distal end 52 is received in the handle cavity 22 for reciprocating movement of this portion of the sleeve through the cavity.

A finger tab 54 is positioned in the handle cavity 22 and is secured to the sleeve. The finger tab 54 has a shank portion 56 that extends into the handle cavity 22. The shank portion 56 has a transverse hole 58 extending through a bottom portion of the shank portion. A portion of the sleeve 44 adjacent the sleeve distal end 52 extends through the transverse hole 58 of the finger tab 54. An internally threaded hole 62 extends downwardly through the finger tab shank portion 56. A set screw 64 is screw threaded into the internally threaded hole 62 and engages against a side of the sleeve 44 to securely connect the finger tab 54 to the sleeve 44. A finger button 66 is provided at the top of the finger tab shank portion 56. The shank portion 56 positions the finger button 66 outwardly from the exterior surface of the handle 12 where the surgeon's hand holding the handle 12 can easily manipulate the finger button 66.

The finger tab 54 can be moved through the length of the handle cavity 22 between a rearward position of the finger tab where the finger tab is adjacent the cavity rearward end 24 as shown in FIG. 2, and a forward position of the finger tab where the finger tab is positioned adjacent the cavity forward end 26 as shown in FIG. 1. As the finger tab 54 is moved between the rearward and forward positions, the sleeve 44 is reciprocated in the handle interior bore 18 and in the cavity 22. The finger tab 54 moves the sleeve 44 toward the handle distal end 16 when the finger tab 54 is moved from the rearward position shown in FIG. 2 toward the forward position shown in FIG. 1. The finger tab 54 moves the sleeve 44 toward the handle proximal end 14 when the finger tab 54 is moved from the forward position shown in FIG. 1 to the rearward position shown in FIG. 2.

A laser optic fiber 72 having an elongate length with opposite proximal 74 and distal 76 ends extends through the handle 12, through the sleeve 44, and through the tip 32. A connector 78 is provided at the laser optic fiber proximal end 74. The connector 78 is adapted for connecting the laser optic fiber 72 to a separate laser light source to transmit laser light through the laser optic fiber to the laser optic fiber distal end 76. The laser optic fiber 72 extends through the handle interior bore 18, through the sleeve interior bore 46, and through the tip interior bore 34 to the laser optic fiber distal end 76 positioned adjacent the tip distal end 38.

A portion of the laser optic fiber 72 is secured to the interior of the sleeve 44 by an epoxy or other equivalent means. The remainder of the laser optic fiber 72 is free to reciprocate through the handle interior bore 18 and through the tip interior bore 34 on movement of the finger tab 54 and the sleeve 44. When the finger tab 54 is moved to the rearward position shown in FIG. 1, the laser optic fiber distal end 76 is positioned adjacent the tip distal end 38. When the finger tab 54 is moved toward the forward position as shown in FIG. 1, a portion of the laser optic fiber adjacent the laser optic fiber distal end 76 is extended or projected from the tip distal end 38 as shown in FIG. 1.

An illumination optic fiber 82 having a length with opposite proximal 84 and distal 86 ends extends through the handle 12, through the sleeve 44 and through the tip 32. The illumination optic fiber proximal end 84 is adapted to be connected to a separate illumination light source to transmit illumination light through the illumination optic fiber 82 to the illumination optic fiber distal end 86. The illumination optic fiber distal end 86 is positioned adjacent the tip distal end 38. The illumination optic fiber 82 is secured stationary in the interior of the tip 32 and in the interior of the handle 12 by adhesives or other equivalent means. A passage way 92 is provided through the adhesive in the sleeve 44 that secures the sleeve to the laser optic fiber 72. The illumination optic fiber 82 extends through the passageway 92, enabling the sleeve 44 and the laser optic fiber 72 to be reciprocated relative to the stationary illumination optic fiber 82 on manual manipulation of the finger tab 54.

In use of the surgical instrument, the laser optic fiber proximal end 74 is connected to a source of laser light and the illumination optic fiber proximal end 84 is connected to a source of illumination light. With the finger tab 54 in the rearward position shown in FIG. 2, both the laser optic fiber distal end 76 and the illumination optic fiber distal end 86 are positioned inside the tip 32 adjacent the tip distal end 38.

The tip 32 is then inserted through a cannula positioned in an incision in the eye, or is inserted directly through the incision. The tip is positioned in the eye with the tip distal end 38 positioned relative to the surgical site to provide the desired area of illumination from the illumination light transmitted from the illumination optic fiber distal end 86. Moving the tip distal end 38 closer to the surgical site reduces the area illuminated by the illumination optic fiber 82. Pulling the tip distal end 38 back away from the surgical site expands the area of illumination by the illumination optic fiber 82.

With the desired area of the surgical site illuminated, the finger tab 54 can then be moved from its rearward position shown in FIG. 2, toward the forward position shown in FIG. 1. The finger pad is gradually manipulated by the hand of the surgeon, causing a portion of the laser optic fiber adjacent the laser optic fiber distal end 76 to be gradually extended from the tip distal end 38. This process is continued until the laser optic fiber distal end 76 is positioned at a desired position relative to the surgical site to begin the surgical procedure. When the surgical procedure is completed, the finger tab 54 is moved by the surgeon's hand to the rearward position of the finger tab. This retracts the portion of the laser optic fiber extended from the tip distal end 38 back into the tip 32. The tip 32 may then be removed from the eye.

Figure 7:
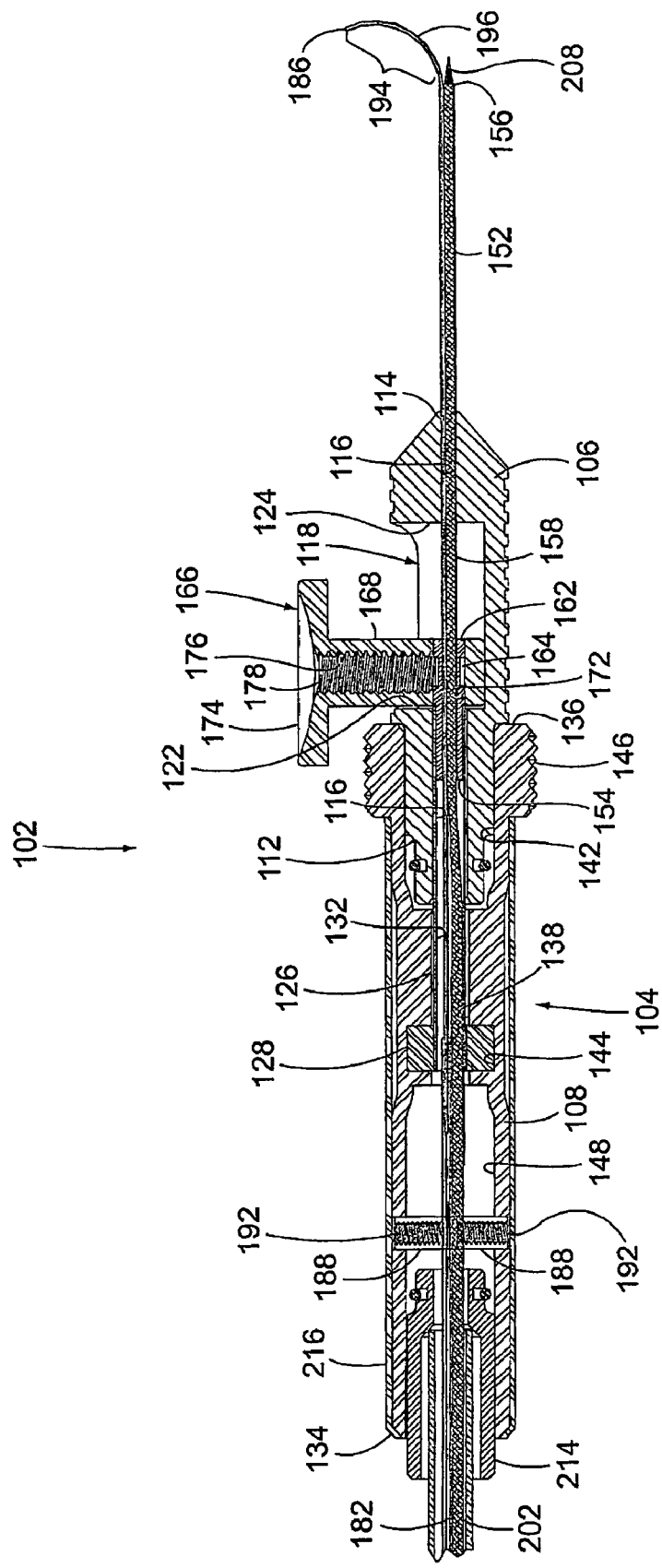

FIGS. 5-7 show a further embodiment of the surgical instrument 102 of the invention. The surgical instrument 102 shown in FIGS. 5-7 is similar to the surgical instrument of U.S. Pat. No. 6,572,608 titled Directional Laser Probe, in that it is capable of directing laser light at a surgical site. In addition, the surgical instrument 102 of FIGS. 5-7 also provides a wide field of illumination at the surgical site.

The surgical instrument 102 is provided with an elongate, narrow handle or hand-piece 104 comprised of a forward piece 106 and a rearward piece 108. The forward piece 106 and rearward piece 108 are mounted to each other for relative rotation.

The forward piece 106 has a length with opposite proximal 112 and distal 114 ends. A center bore 116 extends through the forward piece between its proximal end 112 and its distal end 114. A cavity 118 is recessed into an exterior surface of the forward piece 106. The cavity 118 intersects with the center bore 116. The cavity 118 extends along a portion of the length of the forward piece 106 between a rearward or proximal end 122 of the cavity and a forward or distal end 124 of the cavity.

A tube 126 is secured in the forward piece center bore 116 at the forward piece proximal end 112. The tube 126 projects from the forward piece proximal end 112 to an annular stop 128 secured to an end of the tube. The tube 126 has a center bore 132 that is aligned with the handle forward piece center bore 116.

The handle rearward piece 108 has a length with opposite proximal 134 and distal 136 ends. A center bore 138 extends through the handle rearward piece 108. A portion of the rearward piece center bore 142 adjacent the rearward piece distal end 136 is enlarged and receives a portion of the forward piece at the forward piece proximal end 112. The rearward piece center bore 138 is also formed with an annular groove 144 that receives the annular stop 128 of the handle forward piece tube 126. This mounts the handle forward piece 106 to the handle rearward piece 108 for relative rotation between the two pieces of the handle. The exterior surface of the handle rearward piece 108 is provided with a knurled ring 146 to facilitate manual rotation of the handle rearward piece 108 relative to the handle forward piece 106. The rearward piece center bore is provided with an additional enlarged portion 148 adjacent the rearward piece proximal end 134.

An elongate tubular tip 152 extends through a portion of the handle forward piece center bore 116 and cavity 118 and projects from the handle forward piece distal end 114. The tip 152 has a straight length that extends between opposite proximal 154 and distal 156 ends of the tip. A center bore 158 extends through the tip length. The tip 152 is received in the handle forward piece center bore 116 and in the handle cavity 118 for reciprocating movement of the tip 152 in the center bore 116 and cavity 118.

A tubular collar 162 is mounted on the exterior surface of the tip 152 adjacent the tip proximal end 154. The collar 162 has an annular groove 164 formed in the exterior surface of the collar. The tubular collar 162 reciprocates with the tip 152 in the handle forward piece center bore 116 and cavity 118.

A finger tab 166 is mounted on the tubular collar 162. The finger tab 166 has a shank 168 with a transverse hole 172 that receives the tubular collar 162. A finger button or finger pad 174 is provided at the top of the shank 168. The shank 168 positions the finger pad 174 where it can be easily accessed by a finger of the surgeon's hand holding the handle 104 of the instrument. An internally threaded hole 176 extends through the shank 168 to the transverse hole 172. A set screw 178 is screw threaded into the internally threaded hole 176. The set screw 178 has a projection at its bottom that is received in sliding engagement in the tubular collar groove 164. The engagement of the set screw 178 in the collar groove 164 mounts the finger tab 166 to the tubular collar 162 for relative rotational movement between the tubular collar 162 and the finger tab 166. The engagement of the set screw 178 in the tubular collar groove 164 causes the tubular collar 162 and the tubular tip 152 to reciprocate through the handle forward piece cavity 118 and through the handle forward piece center bore 116 on reciprocating movement of the finger tab 166 in the cavity 118 between the cavity proximal end 122 and the cavity distal end 124.

A laser optic fiber 182 having an elongate length with opposite proximal 184 and distal 186 ends extends through the handle rearward piece center bore 138, through the handle forward piece center bore 116, and through the tubular tip 152.

A pair of diametrically opposed internally threaded tubes 188 extend into the enlarged portion of the handle rearward piece center bore 148 that is adjacent the handle rearward piece proximal end 148. The tubes 188 are positioned on opposite sides of the laser optic fiber 182. A pair of set screws 192 are screw threaded into the internally threaded tubes 188 and engage against opposite sides of the laser optic fiber 182, securing the laser optic fiber stationary relative to the handle rearward piece 108. The set screws 192 prevent the laser optic fiber 182 from rotating relative to the handle rearward piece 108, and prevent the laser optic fiber 182 from moving through the center bore 138 of the handle rearward piece 108 and the center bore 116 of the handle forward piece 106.

With the finger tab 166 moved adjacent the cavity rearward or proximal end 122, the tubular tip 152 is moved to a retracted position relative to the instrument handle 104 and a distal end portion 194 of the laser optic fiber 182 projects from the tubular tip distal end 156. The laser optic fiber distal end portion 194 has a curved configuration as shown in FIGS. 5 and 7. In the preferred embodiment, a sleeve of a shape memory material 196, for example nitinol, is secured over the laser optic fiber distal end portion 194 to give this portion of the laser optic fiber its curved configuration. The laser optic fiber proximal end 184 is provided with a connector 198 that is adapted to connect the optic fiber to a laser light source for transmission of laser light through the length of the laser optic fiber 182 to the laser optic fiber distal end 186.

An elongate illumination optic fiber 202 having opposite proximal 206 and distal 208 ends extends through the handle rearward piece center bore 138, through the handle forward piece center bore 116, and through the tubular tip 152. The illumination optic fiber 202 is secured by adhesives or other equivalent means to the interior of the tubular tip 152. Thus, the illumination optic fiber 202 reciprocates through the handle rearward piece center bore 138 and the handle forward piece center bore 116 on movements of the finger tab 166 and the tubular tip 152 through the handle cavity 118. Although a portion of the illumination optic fiber 202 is secured in the tubular tip 152, the portion of the laser optic fiber 182 that extends through the tubular tip 152 is free to slide through the length of the tubular tip 152 and is free to rotate in the tubular tip 152.

As seen in FIGS. 5-7, the illumination optic fiber distal end 208 has a tapered or conical configuration. This shape of the illumination optic fiber distal end 208 provides a wide field of illumination. The opposite proximal end 206 of the illumination optic fiber 202 is provided with a connector 212 that is adapted to connect to an illumination light source to transmit illumination light through the length of the illumination optic fiber 202 to the illumination optic fiber distal end 208.

A sealing plug 214 is inserted into the enlarged portion 148 of the handle rearward piece center bore 138, closing this end of the bore.

A cylindrical cover 214 is assembled over the exterior surface of the handle rearward piece 108, giving the handle an aesthetically pleasing appearance.

In use of the surgical instrument 102 of FIGS. 5-7, the laser optic fiber connector 198 is first connected to a laser light source and the illumination optic fiber connector 212 is connected to a source of illumination light. The finger tab 166 is pushed to its forward position adjacent the cavity distal end 124 to cause the distal end portion 194 of the laser optic fiber 182 to be retracted into the tubular tip 152 as shown in FIG. 6. The tip 152 is then inserted through a cannula positioned in an incision in the eye, or is inserted directly through the incision. The tubular tip distal end 156 and the illumination optic fiber distal end 208 are positioned close to the desired surgical site, whereby the illumination light transmitted by the illumination optic fiber distal end 208 illuminates the surgical site.

The finger tab 166 is then gradually moved rearwardly toward the cavity proximal end 122 causing the distal end portion of the laser optic fiber 194 to the gradually extended from the tip distal end 156. The handle forward piece 106 and handle rearward piece 108 can be rotated relative to each other to position the curvature of the laser optic fiber distal end portion 194 at a desired position of the surgeon relative to the surgical site. Once the proper location of the laser optic fiber distal end 186 is achieve, laser energy can then be delivered to the surgical site of interest.

Retraction of the laser optic fiber distal end portion 194 is performed by pushing the finger tab 166 forward from its rearward position adjacent the cavity proximal end 122 toward the cavity distal end 124. This causes the tubular tip 152 to straighten the laser optic fiber distal end portion 194 as it retracts the distal end portion into the tubular tip. With the laser optic fiber 182 contained in the tubular tip 152, the tip is then pulled back through the surgical entry site.

Thus, as discussed above, the surgical instruments of the present invention provide a source of laser light for performing surgery and a source of illumination where the illuminated area of the surgical site can be adjusted, and where the direction of the laser light can be adjusted.

Although a specific embodiment of the invention has been described herein, it should be understood that other modifications and variations may be made to the invention without departing from the intended scope of protection provided by the following claims.

What is claimed is:

1. A surgical instrument that provides both illumination light and laser light to a surgical site, the surgical instrument comprising:

a manually manipulatable handle;

a tubular tip secured to the handle, the tip projecting from the handle to a distal end of the tip;

an illumination optic fiber having a length with opposite proximal and distal ends, the illumination optic fiber extending through the handle and the tip to the illumination optic fiber distal end positioned adjacent the tip distal end, the illumination optic fiber being secured stationary relative to the tip;

a laser optic fiber having a length with opposite proximal and distal ends, the laser optic fiber extending through the handle and the tip to the laser optic fiber distal end positioned adjacent the tip distal end and the illumination optic fiber distal end;

a mechanism on the handle, the mechanism being operatively connected to the laser optic fiber to move the laser optic fiber through the handle and the tip between a retracted position of the laser optic fiber where the laser optic fiber distal end is positioned adjacent the tip distal end and the illumination optic fiber distal end, and an extended position of the laser optic fiber where the laser optic fiber distal end is extended from the tip distal end and the illumination optic fiber distal end;

a portion of the laser optic fiber adjacent the laser optic fiber distal end having a curved configuration; and, curved sleeve is mounted on the laser optic fiber distal end portion, and the curved sleeve holds the laser optic fiber distal end portion in the curved configuration.

2. The surgical instrument of claim 1, further comprising: the illumination optic fiber having a tapered tip at the illumination optic fiber distal end.

3. The surgical instrument of claim 2, further comprising: the illumination optic fiber tapered tip projecting outwardly from the tip distal end.

4. The surgical instrument of claim 2, further comprising: the illumination optic fiber tapered tip having a conical configuration.

5. A surgical instrument that provides both illumination light and laser light to a surgical site, the surgical instrument comprising:

a manually manipulatable handle;

a tubular tip secured to the handle, the tip projecting from the handle to a distal end of the tip;

an illumination optic fiber having a length with opposite proximal and distal ends, the illumination optic fiber extending through the handle and the tip to the illumination optic fiber distal end positioned adjacent the tip distal end, the illumination optic fiber being secured stationary relative to the tip;

a laser optic fiber having a length with opposite proximal and distal ends, the laser optic fiber extending through the handle and the tip to the laser optic fiber distal end positioned adjacent the tip distal end and the illumination optic fiber distal end;

a mechanism on the handle, the mechanism being operatively connected to the laser optic fiber to move the laser optic fiber through the handle and the tip between a retracted position of the laser optic fiber where the laser optic fiber distal end is positioned adjacent the tip distal end and the illumination optic fiber distal end, and an extended position of the laser optic fiber where the laser optic fiber distal end is extended from the tip distal end and the illumination optic fiber distal end;

the handle having a forward piece and a rearward piece, the rearward piece being connected to the forward piece for relative rotation of the forward piece and the rearward piece;

the tip being mounted on the handle forward piece for relative movement of the tip and the handle forward piece; and, the mechanism being on the handle forward piece.

6. The surgical instrument of claim 5, further comprising: the illumination optic fiber and the laser optic fiber are secured to the handle rearward piece for rotation of the illumination optic fiber and the laser optic fiber with the handle rearward piece relative to the handle forward piece and the tip.

7. A surgical instrument that provides both illumination light and laser light to a surgical site, the surgical instrument comprising:

an elongate handle having opposite proximal and distal ends, the handle having an interior bore with an interior surface extending through the handle from the handle proximal end to the handle distal end, and the handle having an exterior surface with a cavity recessed into the exterior surface, the cavity intersecting the handle center bore and having opposite proximal and distal ends;

an elongate tubular tip having opposite proximal and distal ends, the tip having an interior bore with an interior surface extending through the tip from the tip proximal end to the tip distal end, the tip proximal end being secured in the handle interior bore at the handle distal end;

an elongate sleeve having opposite proximal and distal ends, the sleeve having an interior bore that extends through the sleeve between the sleeve proximal and distal ends, the sleeve being mounted in the handle interior bore and in the handle cavity for reciprocating movement of that sleeve through the handle interior bore and the handle cavity;

a finger tab in the handle cavity and secured to the sleeve, the finger tab extending out of the handle cavity and beyond the handle exterior surface, the finger tab being movable in the handle cavity between a rearward position where the finger tab is adjacent the cavity proximal end, and a forward position where the finger tab is adjacent the cavity distal end, the finger tab moving the sleeve toward the handle distal end when the finger tab is moved from the rearward position to the forward position, and the finger tab moving the sleeve toward the handle proximal end when the finger tab is moved from the forward position to the rearward position;

an illumination optic fiber having a length with opposite proximal and distal ends, the illumination optic fiber proximal end being adapted to be attached to a separate illumination light source to transmit illumination light through the illumination optic fiber to the illumination optic fiber distal end, the illumination optic fiber extending through the handle interior bore, through the sleeve interior bore, and through the tip interior bore to the illumination optic fiber distal end positioned adjacent the tip distal end, the illumination optic fiber being secured stationary relative to the handle and the tip; and a laser optic fiber having a length with opposite proximal and distal ends, the laser optic fiber proximal end being adapted to be attached to a separate laser light source to transmit laser light through the laser optic fiber to the laser optic fiber distal end, the laser optic fiber extending through the handle interior bore, through the sleeve interior bore, and through the tip interior bore to the laser optic fiber distal end positioned adjacent the tip distal end when the finger tab is in the rearward position, the laser optic fiber being secured to the sleeve, and a portion of the laser optic fiber adjacent the laser optic fiber distal end being extended from the tip distal end when the finger tab is moved from the rearward position toward the forward position.

8. The surgical instrument of claim 7, further comprising:
the illumination optic fiber having a tapered tip at the illumination optic fiber distal end.

9. The surgical instrument of claim 8, further comprising:
the illumination optic fiber tapered tip projecting outwardly from the tip distal end.

10. The surgical instrument of claim 8, further comprising:
the illumination optic fiber tapered tip having a conical configuration.

11. The surgical instrument of claim 7, further comprising:
a portion of the laser optic fiber adjacent the laser optic fiber distal end having a curved configuration.

12. The surgical instrument of claim 11, further comprising:
a curved sleeve is mounted on the laser optic fiber distal end portion, and the curved sleeve holds the laser optic fiber distal end portion in the curved configuration.

13. The surgical instrument of claim 7, further comprising:
the handle having a forward piece and a rearward piece, the rearward piece being connected to the forward piece for relative rotation between the forward piece and the rearward piece;
the tip being mounted on the handle forward piece for relative movement of the tip and the handle forward piece; and,
the finger tab and cavity being on the handle forward piece.

14. The surgical instrument of claim 13, further comprising:
the illumination optic fiber and the laser optic fiber are secured to the handle rearward piece for rotation of the illumination optic fiber and the laser optic fiber with the handle rearward piece relative to the handle forward piece and the tip.

* * * * *